United States Patent [19]

Dittmann

[11] Patent Number: 5,810,002

[45] Date of Patent: Sep. 22, 1998

[54] RESPIRATOR

[75] Inventor: Ralf Dittmann, Lübeck, Germany

[73] Assignee: Drägerwerk AG, Lübeck, Germany

[21] Appl. No.: 799,613

[22] Filed: Feb. 12, 1997

[30] Foreign Application Priority Data

Sep. 26, 1996 [DE] Germany .................. 196 39 522.4

[51] Int. Cl.⁶ .................................................. A61M 16/00
[52] U.S. Cl. ........................ 128/203.12; 128/203.14; 128/203.25; 128/205.13
[58] Field of Search ..................... 128/204.21, 204.18, 128/203.12, 200.24, 205.13, 203.14, 203.25

[56] References Cited

U.S. PATENT DOCUMENTS

| | | | |
|---|---|---|---|
| 3,923,056 | 12/1975 | Bingmann et al. | 128/204.21 |
| 4,313,436 | 2/1982 | Schwanbom et al. | 128/203.12 |
| 4,702,242 | 10/1987 | Broddner et al. | 128/205.13 |
| 4,909,246 | 3/1990 | Kiske et al. | 128/205.14 |
| 5,253,640 | 10/1993 | Falb et al. | 128/203.12 |
| 5,490,499 | 2/1996 | Heinonen et al. | 128/203.28 |
| 5,509,406 | 4/1996 | Kock et al. | 128/203.12 |
| 5,615,669 | 4/1997 | Olsson et al. | 128/203.12 |
| 5,619,986 | 4/1997 | Werner et al. | 128/203.12 |

FOREIGN PATENT DOCUMENTS

| | | |
|---|---|---|
| 38 20 165 C2 | 4/1990 | Germany . |
| 92 18 160 | 8/1993 | Germany . |
| 34 22 066 | 12/1995 | Germany . |

Primary Examiner—John G. Weiss
Assistant Examiner—V. Srivastava
Attorney, Agent, or Firm—McGlew and Tuttle

[57] ABSTRACT

A respirator with a breathing gas delivery unit having a variable delivery volume, with a breathing circuit having an inspiration branch and an expiration branch, and with a feed line for breathing gas. The feed line opens into the breathing circuit and is connected to a metering unit. Especially good mixing is achieved within the breathing circuit for high and low flow rates to be metered into the breathing circuit. The feed line has a branching point with a branch line, and the lines are connected to the inspiration branch and to the expiration branch such that the feeding in of breathing gas into the inspiration branch and/or into the expiration branch is made possible.

9 Claims, 1 Drawing Sheet

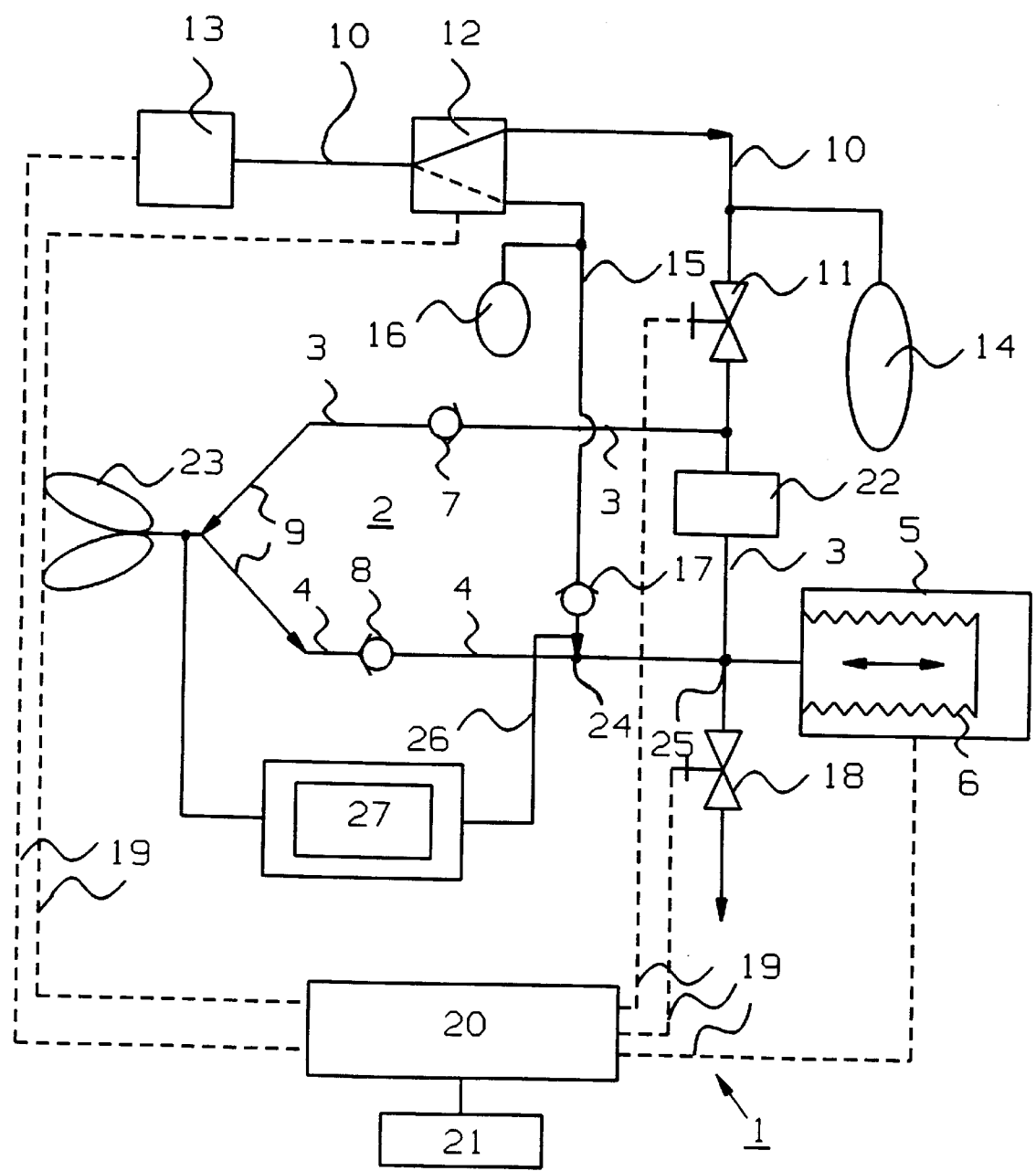

RESPIRATOR

FIELD OF THE INVENTION

The present invention pertains to a respirator with a breathing gas delivery unit having a variable delivery volume, with a breathing circuit having an inspiration branch and an expiration branch, with a feed line for breathing gas, which opens into the breathing circuit and is connected to a metering unit, and with a control unit actuating the breathing gas delivery unit.

BACKGROUND OF THE INVENTION

In prior-art respirators with the possibility of rebreathing, part of the expired gas or the total amount of the expired gas is returned into the breathing circuit and is fed again to the patient by the breathing gas delivery unit at the time of the next breathing strokes after the exhaled carbon dioxide has been removed from it and it has been enriched with fresh breathing gas. The breathing gas delivery unit of the respirator draws in the breathing gas from the expiration branch during a breathing stroke and empties it into the inspiration branch. The breathing gas delivery unit is usually provided for this purpose with a variable volume, e.g., in the form of a bellows or of a piston movable in a cylinder. A respirator of this type has become known from DE 38 20 165 C2. It is particularly important in the prior-art respirator for the composition of the breathing gas to remain possibly constant within the breathing circuit and for the fresh breathing gas fed in to be utilized as well as possible. The fresh breathing gas is usually fed into the inspiration branch of the breathing circuit, while excess breathing gas is released after each expiration stroke via a discharge valve. The prior-art breathing gas feed into the inspiration branch is advantageous if the amount of breathing gas fed in is markedly larger than the breathing gas consumption by the patient. Particularly rapid mixing within the breathing circuit is achieved because of the relatively large amount of breathing gas fed into the breathing circuit. However, if the amount of breathing gas fed in is markedly reduced, e.g., below 1 L/minute, and the qualitative composition of the breathing gas is also changed additionally, it may happen that the breathing gas fed in will be drawn in by the breathing gas delivery unit only incompletely. It will reach the patient directly, instead, at the time of the next inspiration stroke. Due to the insufficient mixing of the breathing gas within the breathing circuit, the patient receives a nonuniform concentration profile of the breathing gas composition.

If breathing gas is metered into the breathing circuit by means of a closed control loop in such a case by measuring the qualitative composition of the gas in the inspiration branch in the vicinity of the patient connection and changing the composition of the breathing gas or the breathing gas flow corresponding to the deviation of the actual value from a set point, hunting may occur, which will additionally increase the variations in the concentration profile.

SUMMARY AND OBJECTS OF THE PRESENT INVENTION

The primary object of the present invention is to improve a respirator of this type such that an especially uniform concentration profile of the breathing gas composition is achieved within the breathing circuit at different amounts of breathing gas fed into the breathing circuit.

According to the invention, a respirator is provided with a breathing gas delivery unit having a variable delivery volume and with a breathing circuit having an inspiration branch and an expiration branch. A feed line is provided for breathing gas, which opens into the breathing circuit and is connected to a metering unit. A control unit actuates the breathing gas delivery unit. The feed line has a branching point with a branch line, and the feed and branch lines are connected to the inspiration branch and to the expiration branch such that the feeding of breathing gas from the metering unit into the inspiration branch and/or into the said expiration branch is made possible.

The advantage of the present invention is essentially that the breathing gas is fed into the inspiration branch in the case of a correspondingly large amount of breathing gas, as in the prior-art respirator, but the breathing gas is fed into the expiration branch in the case of the metering of small amounts of breathing gas, e.g., below 1.5 L/minute, so that the fresh breathing gas is first drawn in directly from the breathing gas delivery unit and it is then delivered into the inspiration line through the carbon dioxide absorber during the next inspiration stroke. Especially good mixing of the fresh breathing gas with the breathing gas present in the breathing circuit is thus achieved, on the one hand, and, on the other hand, the fresh breathing gas is additionally humidified in the carbon dioxide absorber.

The branching point is preferably designed as a reversing valve that draws off the breathing gas either through the feed line or through the branch line. The reversing valve is preferably actuated by the control unit such that if an amount of breathing gas below a predetermined limit value is set at the metering unit, the breathing gas is fed into the expiration branch preferably via at least one of the lines, and it is preferably fed into the said inspiration branch above the predetermined limit value.

The branch line preferably opens into the breathing circuit at a point of entry between an expiration valve located in the expiration branch and a drain valve. A return line of a draining gas-measuring device is preferably connected to the point of entry.

One exemplary embodiment of the present invention is shown in the FIGURE and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic circuit diagram of the respirator according to the invention.

DESCRIPTION OF THE PREFERRED EMBODIMENT

Referring to the drawings in particular, the respirator 1 shown in the only FIGURE has a breathing circuit 2, which is divided into an inspiration branch 3 and an expiration branch 4. The breathing gas is circulated by a breathing gas delivery unit 5 with a bellows 6 acting as a variable delivery volume. The direction of circulation in the breathing circuit 2 is determined by an inspiration valve 7 and an expiration valve 8. The direction of flow in the breathing circuit is illustrated by direction arrows 9. A feed line 10, which is connected to a metering unit 13 for breathing gas via a shut-off valve 11 and a reversing valve 12, opens into the inspiration branch 3. A gas reservoir 14 in the form of an elastic bag is connected to the feed line 10 upstream of the shut-off valve 11. The reversing valve 12 is connected to a branch or another feed line 15, through which breathing gas is sent from the metering unit 13 via a buffer volume 16 and a nonreturn valve 17 into the expiration branch 4. Excess breathing gas is released into an anesthetic gas discharge line, not shown in the FIGURE, via a drain valve 18 located in the connection area between the inspiration branch 3 and the expiration branch 4. The valves 11, 12, 18, the metering unit 13, and the breathing gas delivery unit 5 connected via signal lines 19 to a central control unit 20, which generates the control commands needed for respiration and into which the breathing parameters set at an input unit 21, e.g., the amount of breathing gas, stroke volume and breathing frequency, are read.

To perform an inspiration stroke, the control unit 20 sends a corresponding control signal to the breathing gas delivery unit 5, and the bellows 6, which has been filled with breathing gas during a preceding expiration, pumps the breathing gas into the symbolically represented lungs 23 of a patient via a carbon dioxide absorber 22 located in the inspiration branch 3 and the inspiration valve 7. The metering unit 13 is connected to the feed line 10 in the switching position of the reversing valve 12 shown. The breathing gas flow set on the metering unit 13 via the control unit 20 flows continuously into the gas reservoir 14. The shut-off valve 11, which is connected to the inspiration branch 3 between the inspiration valve 7 and the carbon dioxide absorber 22, switches over into the open position during the expiration stroke, i.e., during the time interval during which the bellows 6 is being filled with breathing gas, so that the bellows 6 is also able to draw in breathing gas directly from the gas reservoir 14 via the carbon dioxide absorber 22. The shut-off valve 11 closes at the end of the expiration stroke, and the drain valve 18 opens briefly in order to release excess breathing gas that may be present from the breathing circuit 2.

However, if the reversing valve 12 is in the switching position indicated by broken line, the breathing gas flows from the metering unit 13 via the branch line 15 and the nonreturn valve 17 into the expiration line 4. The point 24 at which the branch line 15 opens into the expiration branch 4 is located between the expiration valve 8 and a point 25 of connection of the breathing gas delivery unit 5 to the inspiration branch 3 and to the expiration branch 4. The bellows 6 of the breathing gas delivery unit 5 draws breathing gas from the breathing circuit 2 and from the buffer volume 16 via the nonreturn valve 17 during the phase of expiration. The nonreturn valve 17 is closed during the phase of inspiration by the inspiration pressure building up in the breathing circuit.

The reversing valve 12 is actuated by the control unit 20 as follows:

Based on the breathing parameters set on the input unit 21, the control unit 20 receives the information on what breathing gas flow is to be delivered by the metering unit 13. This breathing gas flow to be metered is compared in the control unit 20 with a limit value being stored there. If the breathing gas flow rate is equal to or greater than the limit value, e.g., $\geq 1.5$ L/minute, the reversing valve 12 is switched into the position shown in the FIGURE (solid line), and the breathing gas flows via the feed line 10 into the inspiration branch 3. However, if the breathing gas flow rate is lower than 1.5 L/minute, the reversing valve 12 is switched over to the gas path indicated by broken line, and the breathing gas is metered via the branch line 15 into the expiration branch 4.

Due to feeding breathing gas into the inspiration branch or into the expiration branch as needed in the respirator 1 according to the present invention, especially good utilization of the fresh breathing gas metered into the breathing circuit is achieved at high and low breathing gas flow rates alike, because the deviations between the breathing gas composition in the breathing circuit 2 and in the feed line 10 are hardly any greater at high breathing gas flow rates. Differences in the qualitative composition of the gas are more pronounced in the case of low breathing gas flow rates, so that good mixing of the breathing gas delivered by the metering unit 13 with the gas present in the breathing circuit 2 is necessary. The good mixing is achieved by the breathing gas being pumped via the branch line 15 first into the bellows 6 and from there into the inspiration branch 3 via the carbon dioxide absorber 22.

It is especially advantageous to connect the return line of a gas-measuring device 27 measuring by draining at the point of entry 24. The point of entry 24, which is present for the gas-measuring device 27 anyway, can thus also be used for feeding in the breathing gas.

While a specific embodiment of the invention has been shown and described in detail to illustrate the application of the principles of the invention, it will be understood that the invention may be embodied otherwise without departing from such principles.

What is claimed is:

1. A respirator, comprising:
   a breathing gas delivery unit having a variable delivery volume;
   a breathing circuit having an inspiration branch and an expiration branch;
   a feed line for breathing gas, which opens into said breathing circuit;
   a metering unit connected to said feed line;
   a control unit for actuating said breathing gas delivery unit; and
   a branch line connected at one end to said feed line at a branching point with another end of said branch line connected to one of said expiration branch and said inspiration branch, and said feed line connected to the other of said expiration branch and said inspiration branch, such that the feeding of breathing gas from said metering unit into said inspiration branch and/or into said expiration branch is made possible.

2. A respirator in accordance with claim 1, wherein said branching point includes a reversing valve that draws off the breathing gas either through said feed line or through said branch line.

3. A respirator in accordance with claim 2 wherein said reversing valve is actuated by said control unit such that if an amount of breathing gas below a predetermined limit value is set at said metering unit, the breathing gas is fed into said expiration branch via at least one of said feed line and said branch line, and the breathing gas is fed into said inspiration branch above said predetermined limit value.

4. A respirator in accordance with claim 1, wherein said expiration branch includes an expiration valve and said breathing circuit is connected to a drain valve and said branch line opens into said breathing circuit at a point of entry between said expiration valve and said drain valve.

5. A respirator in accordance with claim 4, wherein a return line of a draining gas-measuring device is connected to said point of entry.

6. A respirator, comprising:

a metering unit for delivering a variable amount of breathing gas;

a breathing circuit having an inspiration branch and an expiration branch;

a feed line for feeding breathing gas from said metering unit to said inspiration branch;

another feed line for feeding breathing gas from said metering unit to said expiration branch;

a control unit for controlling said variable amount of breathing gas delivered by said metering unit and selectively feeding breathing gas through said feed line to said inspiration branch and through said another feed line to said expiration branch.

7. A respirator in accordance with claim 6, wherein:

said control unit feeds said breathing gas into expiration branch when said amount of breathing gas is below a predetermined limit value, said control unit feeds said breathing gas into inspiration branch when said amount of breathing gas is above said predetermined limit value.

8. A respirator in accordance with claim 7, further comprising:

a breathing gas delivery unit for circulating gases from said expiration branch to said inspiration branch, said control unit actuating said breathing gas delivery unit.

9. A respirator in accordance with claim 8, wherein:

said expiration branch includes an expiration valve;

said another feed line opens into said expiration branch between said expiration valve and said breathing gas delivery unit.

* * * * *